US009132260B2

(12) United States Patent
Schaeffer et al.

(10) Patent No.: US 9,132,260 B2
(45) Date of Patent: Sep. 15, 2015

(54) THERAPEUTIC AGENT DELIVERY DEVICE WITH A DUAL BALLOON HAVING DISTAL TAPER APERTURES

(75) Inventors: Darin G. Schaeffer, Bloomington, IN (US); William F. Moore, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1479 days.

(21) Appl. No.: 12/825,965

(22) Filed: Jun. 29, 2010

(65) Prior Publication Data

US 2010/0331817 A1    Dec. 30, 2010

Related U.S. Application Data

(60) Provisional application No. 61/221,111, filed on Jun. 29, 2009.

(51) Int. Cl.
*A61M 25/10* (2013.01)

(52) U.S. Cl.
CPC ......... *A61M 25/1011* (2013.01); *A61M 25/104* (2013.01); *A61M 2025/105* (2013.01); *A61M 2025/1013* (2013.01); *A61M 2025/1052* (2013.01)

(58) Field of Classification Search
CPC ..... A61F 2/91; A61F 2/915; A61F 250/0039; A61F 2002/91533; A61F 2002/91508; A61M 2025/105; A61M 25/1011; A61M 25/104; A61M 2025/1013; A61M 2025/1052; A61L 29/16; A61L 29/085; A61L 31/16; A61K 2700/00
USPC .......................... 604/103.01, 103.02, 101.02, 604/103.06–103.08
See application file for complete search history.

(56) References Cited

U.S. PATENT DOCUMENTS

| 5,049,132 | A | * | 9/1991 | Shaffer et al. ............ 604/101.02 |
| 5,690,642 | A |   | 11/1997 | Osborne et al. |
| 5,814,061 | A |   | 9/1998 | Osborne et al. |
| 7,094,765 | B1 |   | 8/2006 | Iversen et al. |
| 2005/0288632 | A1 | * | 12/2005 | Willard .................... 604/103.01 |
| 2006/0269587 | A1 |   | 11/2006 | Iversen et al. |
| 2009/0254064 | A1 |   | 10/2009 | Boatman |

FOREIGN PATENT DOCUMENTS

| WO | WO 2009/036135 A1 | 3/2009 |
| WO | WO 2009036135 A1 * | 3/2009 |

* cited by examiner

*Primary Examiner* — Theodore Stigell
*Assistant Examiner* — Lauren M Peng
(74) *Attorney, Agent, or Firm* — Brinks Gilson & Lione (57) ABSTRACT

The present disclosure generally provides a multiple balloon assembly used as part of the distal region of a medical device that is capable of delivering a therapeutic agent into a body vessel having bodily fluid. The multiple balloon assembly comprises an inner balloon and an outer balloon. The outer balloon further comprises a proximal taper region, a middle region, and a distal taper region. The inflation of the inner balloon causes the middle region of the outer balloon to contact the inner wall of the body vessel, thereby, occluding the flow of fluid through the body vessel. The proximal taper region and the distal taper region are configured such that they do not touch the inner wall of the body vessel. One of the distal taper and proximal taper regions has a plurality of apertures configured to allow for the therapeutic agent to be delivered into the body vessel at a predetermined rate. A medical device that incorporates the multiple balloon assembly of the present disclosure, as well as a method for using the medical device and multiple balloon assembly are further disclosed.

21 Claims, 5 Drawing Sheets

(Expanded State)

Figure 2A (Collapsed State)

Figure 2B (Expanded State)

Figure 3A (Collapsed State)

Figure 3B (Expanded State)

Figure 4

THERAPEUTIC AGENT DELIVERY DEVICE WITH A DUAL BALLOON HAVING DISTAL TAPER APERTURES

CROSS-REFERENCE TO RELATED APPLICATIONS

This application claims priority to and all available benefits of U.S. Provisional Patent Application No. 61/221,111, filed Jun. 29, 2009, and which is hereby incorporated by reference in its entirety.

FIELD

The present disclosure relates generally to medical devices configured to deliver a therapeutic agent into a body vessel having bodily fluid. More specifically, this disclosure relates to multiple balloon catheters useful in the local administration of a therapeutic agent within a patient and their method of use.

BACKGROUND

Local administration of a therapeutic agent involves the delivery of the agent to a specific organ or location in the body. In comparison, general systemic administration delivers a therapeutic agent to a much larger portion of the body. Thus one benefit associated with local administration over general systemic administration is a reduction in the amount of therapeutic agent lost during the treatment due to the unnecessary exposure of surrounding tissue to the agent. Minimizing the amount of therapeutic agent lost during treatment ultimately results in exposing the patient to a lower dosage of the agent.

Percutaneous delivery systems, such as medical catheter systems, are commonly used for the local administration of therapeutic agents to a desired treatment site within the body vessel through a minimally invasive, surgical procedure. Preferably, once the therapeutic agent is injected into the body vessel, the agent will flow downstream from the point of injection to the target site. This is particularly desirable when the therapeutic agent is a diagnostic agent used as a contrast medium or a mixture of embolization spheres or particles used to treat certain forms of cancer. Since a multiple balloon catheter normally delivers the therapeutic agent along the entire length of the balloon, it is likely that the combination of injection dynamics and fluid rheology will result in the therapeutic agent traveling upstream or away from the desired target, as well as downstream towards the target. Accordingly, there exists a need to provide a percutaneous delivery system that minimizes the loss of a therapeutic agent by enhancing the ability of the therapeutic agent to selectively flow downstream for delivery to the targeted site.

SUMMARY

The present disclosure generally provides a multiple balloon assembly used as part of the distal region of a medical device that is capable of delivering a therapeutic agent into a body vessel having bodily fluid. The medical device includes a catheter that includes an inflation lumen, a therapeutic agent delivery lumen, and a wire guide lumen.

One embodiment of a multiple balloon assembly, constructed in accordance with the teachings of the present disclosure, comprises an inner balloon and an outer balloon both having a first end and a second end. The first end of the inner balloon is in contact with both the wire guide lumen and the inflation lumen, while the second end is in contact with only the wire guide lumen. The inner balloon is also in communication with the inflation lumen and configured to move between a collapsed state and an expanded state. When the inner balloon moves from a collapsed state to the expanded state, the inner balloon forces the outer balloon to contact the wall of the body vessel and to occlude the flow of fluid through the vessel.

The outer balloon, which is disposed around the inner balloon, is in communication with the therapeutic agent delivery lumen. The outer balloon includes a proximal taper region, a middle region, and a distal taper region. The proximal taper region, which includes the first end of the outer balloon, is in contact with the catheter. The middle region is in contact with the inner balloon when the inner balloon is in the expanded state. Finally, the distal taper region, which includes the second end of the outer balloon, is in contact with the wire guide lumen. One of the distal taper and proximal taper regions has a plurality of apertures configured to allow for the therapeutic agent to be delivered into the body vessel.

According to one aspect of the present disclosure, the cross-sectional area of the middle section of the outer balloon that can contact the inner wall of the body vessel is large enough to dilate a portion of the body vessel. The proximal taper region and the distal taper region of the outer balloon are configured such that they do not make contact with the inner wall of the body vessel when the middle region makes contact with said inner wall of the body vessel.

According to another aspect of the present disclosure, each aperture in the distal taper region or proximal taper region of the outer balloon is sized and shaped to provide a desired rate of therapeutic agent release from the outer balloon into the body vessel. Preferably, each aperture has a diameter ranging from about 10 micrometers (0.0004 inch) to about 0.5 mm (0.02 inch). The therapeutic agent is preferably one selected from the group of embolization agents, chemotherapy agents, gene therapy agents, alcohols, and diagnostic contrast agents.

Another embodiment of the present disclosure describes a medical device that incorporates and uses the multiple balloon assembly described herein. This medical device, which includes a catheter that defines an inflation lumen, a therapeutic agent delivery lumen, and a wire guide lumen, can occlude the flow of fluid through the body vessel when the movement of the inner balloon from a collapsed state to the expanded state forces the middle region of the outer balloon to contact the wall of the body vessel. The medical device may further comprise a manifold that includes an inflation port in communication with the inflation lumen, a therapeutic agent delivery port in communication with the therapeutic agent delivery lumen, and a wire guide port in communication with the wire guide lumen.

Yet another embodiment of the present disclosure provides a method for delivering a therapeutic agent into a body vessel having bodily fluid. This method generally comprises the steps of introducing into the body vessel, a catheter having an inflation lumen, a therapeutic agent delivery lumen, and a wire guide lumen. A guide wire is then inserted through the wire guide lumen into the body vessel, followed by inserting a multiple balloon assembly as previously described in its collapsed state over the guide wire. The multiple balloon assembly is finally positioned in a location proximate to the target site.

The multiple balloon assembly is allowed to move from the collapsed state to an expanded state by inflating the inner balloon and forcing the middle region of the outer balloon to contact the inner wall of the body vessel. The contact between the middle region and the wall of the vessel is such that the flow of fluid through the body vessel is occluded. A therapeutic agent is then introduced from the delivery lumen into the outer balloon and subsequently delivered into the body vessel through the apertures present in one of the taper regions of the outer balloon. After delivery of the therapeutic agent is complete, the inner balloon is deflated allowing the multiple balloon assembly to move from the expanded state to a collapsed state. The multiple balloon assembly and the rest of the device can then be safely removed from the body vessel.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is in no way intended to limit the present disclosure or its application or uses. It should be understood that throughout the description and drawings, corresponding reference numerals indicate like or corresponding parts and features.

The present disclosure generally provides a multiple-balloon medical device for delivering a therapeutic agent into a body vessel having bodily fluid. This medical device, which extends from a proximal region to a distal region, comprises a catheter, a wire guide, and a multiple balloon assembly. The catheter further defines an inflation lumen, a therapeutic agent delivery lumen, and a wire guide lumen. A guide wire is disposed within the wire guide lumen. The multiple balloon assembly includes an inner balloon and outer balloon attached to the distal region of the wire guide lumen. The inner balloon, which is configured to move between a collapsed state and an expanded state, is in communication with the inflation lumen. The outer balloon is disposed around the inner balloon and is in communication with the therapeutic agent delivery lumen. The outer balloon is further comprised of a proximal taper region, a middle region, and a distal taper region. According to one aspect of the present disclosure, the distal taper region of the outer balloon has a plurality of apertures for delivering the therapeutic agent into the body vessel. However, according to another aspect of the present disclosure, the proximal taper region instead of the distal taper region may include the plurality of apertures.

The movement of the inner balloon to an expanded state results when a fluid is allowed to flow through the inflation lumen. The inflation of the inner balloon forces the middle region of the outer balloon to contact the wall of the body vessel. The contact between the middle region of the outer balloon and the vessel wall occludes the flow of fluid through the vessel. A therapeutic agent is then allowed to flow through the delivery lumen into the space between the inner balloon and outer balloon. The apertures in the distal or proximal taper region of the outer balloon allows for the therapeutic agent to be delivered into the body vessel.

As used within this disclosure, a body vessel having bodily fluid is defined to mean any body passage comprising a lumen through which bodily fluid may flow. Thus a body vessel includes, but is not limited to, blood vessels, esophageal, intestinal, billiary, urethal, and ureteral passages. Preferably, the body vessel is a blood vessel, such as an artery, capillary, or vein.

Figure 1A:
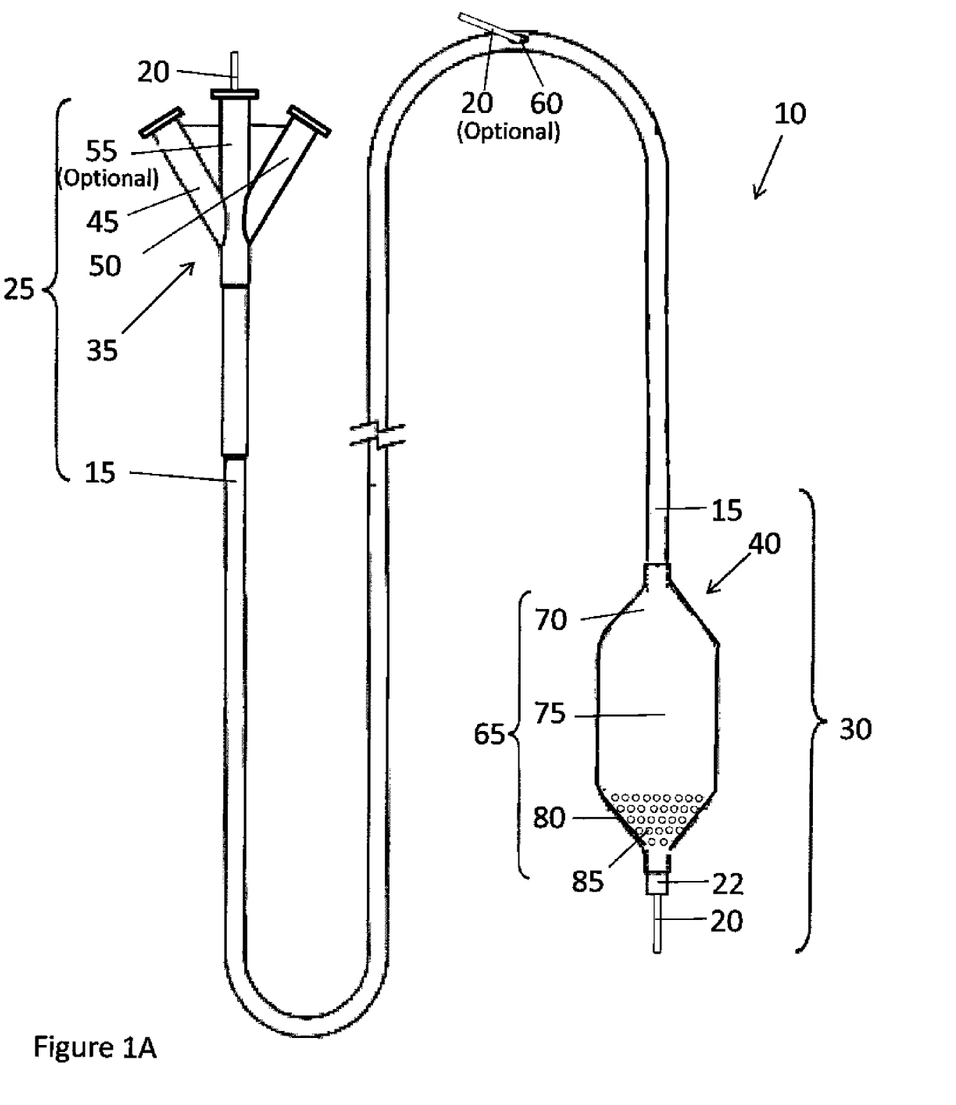
FIG. 1A is a perspective view of a multiple balloon medical device according to the teachings of the present disclosure.
Figure 1B:
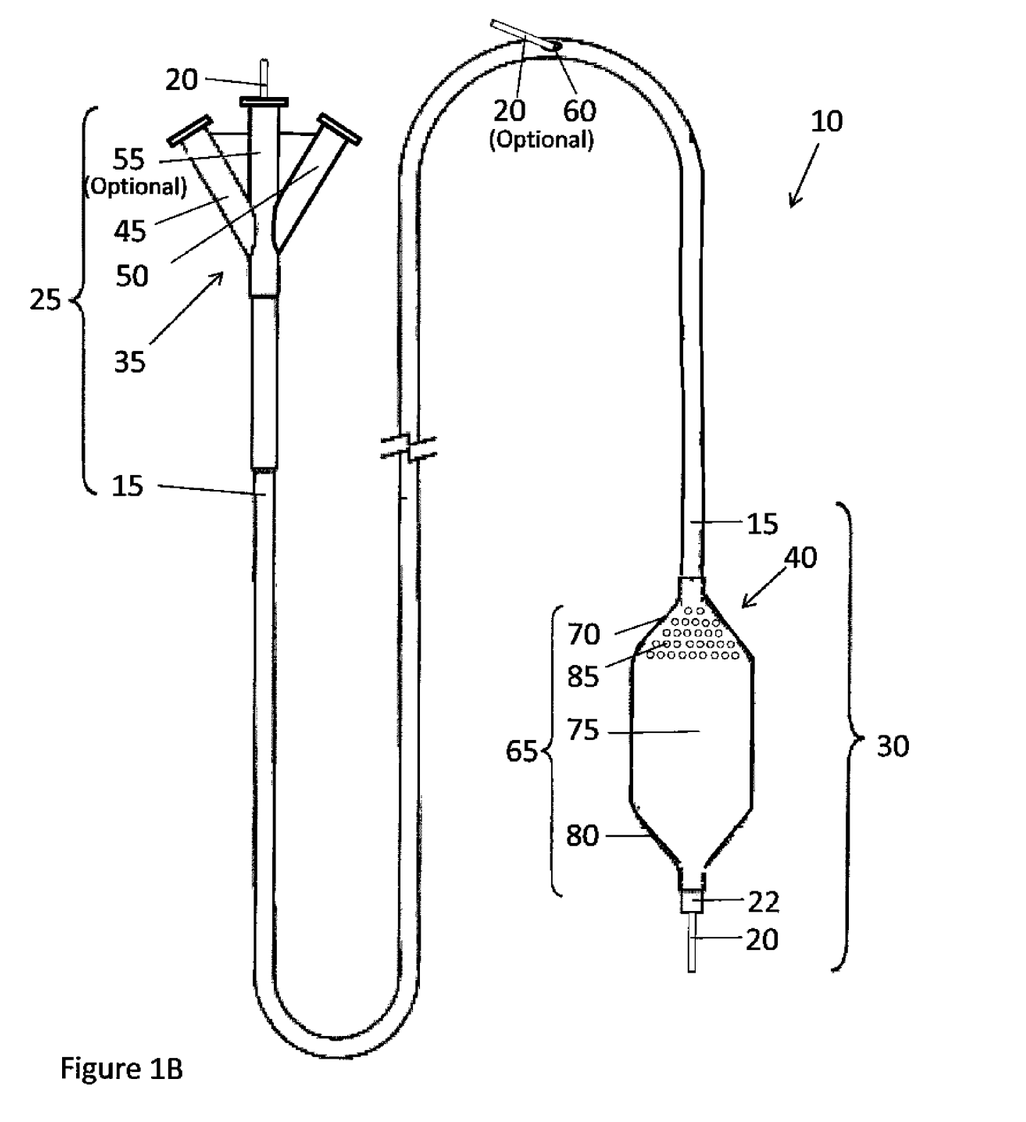
FIG. 1B is a perspective view of a multiple balloon medical device according to another aspect of the present disclosure.

Referring now to FIGS. 1A and 1B, a multiple balloon medical device 10 is described according to one embodiment of the present disclosure. The medical device, which extends from a proximal region 25 to a distal region 30, includes a catheter 15 and a wire guide lumen 22 that extends through at least a portion of the catheter 15. Optionally, a wire guide 20 may be disposed within wire guide lumen 22. The medical device may include a manifold 35 located within the proximal region 25 and a multiple balloon assembly 40 located within the distal region 30. The manifold 35 can include multiple ports, such as an injection port 45, an inflation port 50, and a wire guide port 55 that are connected to a delivery lumen for the therapeutic agent, an inflation lumen, and the wire guide lumen 22, respectively. Each of the lumens are typically housed within the catheter 15. According to one aspect of the present disclosure, the medical device 10 may be described as an "over the wire" system when the wire guide port 55 is included as part of the manifold 35. However, one skilled-in-the-art will understand that the medical device 10 may optionally be a "short wire" system in which the manifold does not include a wire guide port 55, but rather access to the wire guide lumen 22 within the catheter 15 is provided in an intermediate region of the catheter 15 through a port opening 60.

The distal region 30 of the medical device 10 includes a multiple balloon assembly 40 with an outer balloon 65 disposed around an inner balloon. The outer balloon 65 includes a proximal taper region 70, a middle region 75, and a distal taper region 80. According to one aspect of the present disclosure as shown in FIG. 1A, the distal taper region 80 further includes a plurality of holes or apertures 85 through which a therapeutic agent can be released into the body vessel. However, according to another aspect of the present disclosure as shown in FIG. 1B, the proximal taper region 70 rather than the distal taper region 80 may include the plurality of apertures 85 through which the therapeutic agent can be released into the body vessel.

Figure 2A:
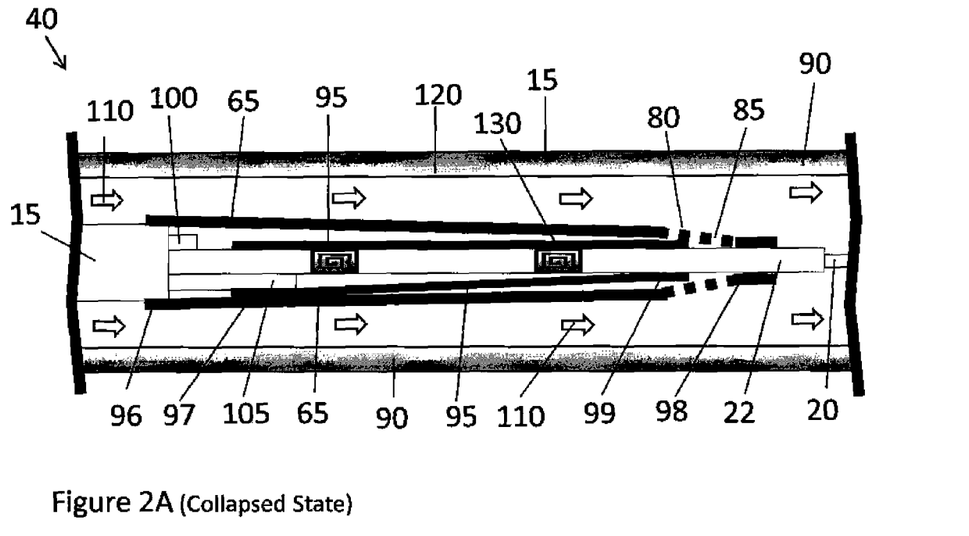
FIG. 2A is a cross sectional view of the multiple balloon assembly of the medical device of FIG. 1A shown in a collapsed state according to one aspect of the present disclosure.
Figure 2B:
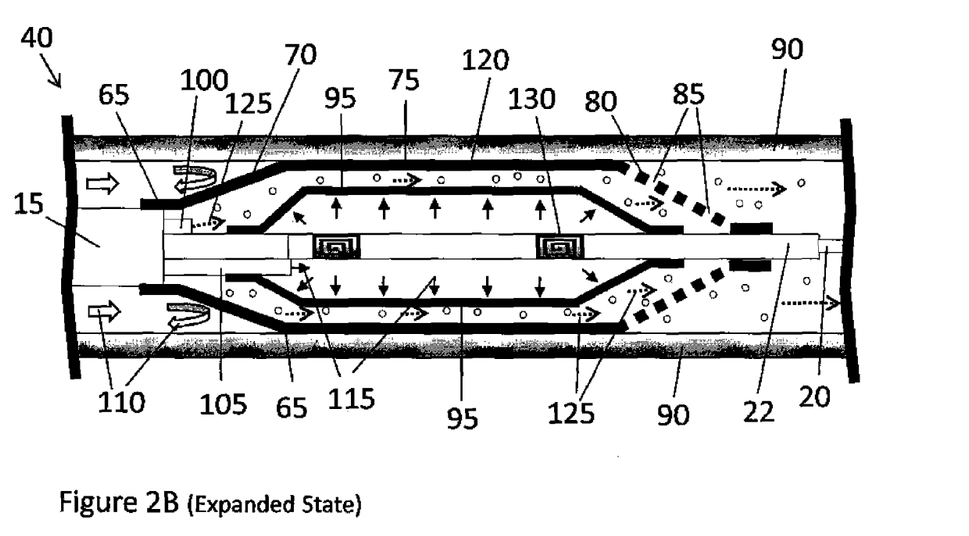
FIG. 2B is a cross sectional view of the multiple balloon assembly of the medical device of FIG. 1A shown in an expanded state according to one aspect of the present disclosure.
Figure 3A:
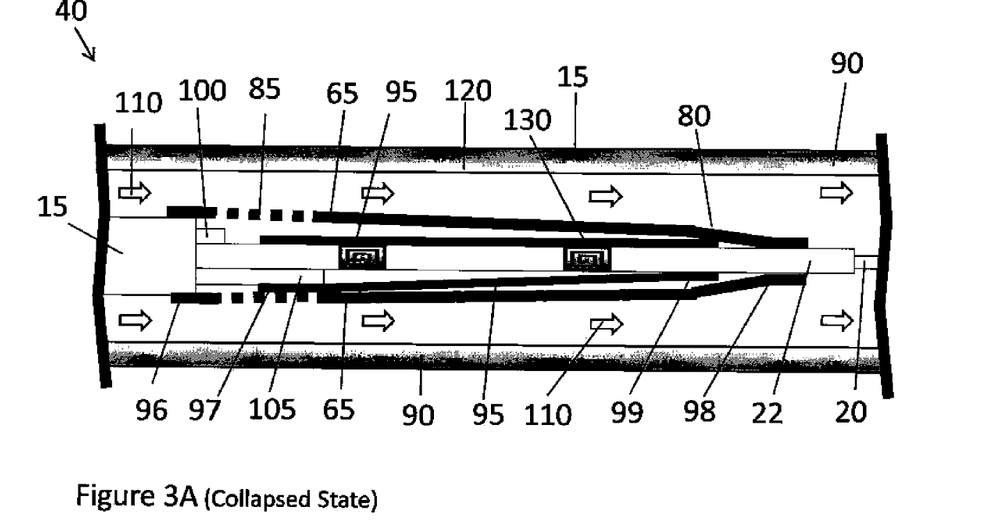
FIG. 3A is a cross sectional view of the multiple balloon assembly of the medical device of FIG. 1B shown in a collapsed state according to another aspect of the present disclosure.

Referring now to FIGS. 2A, 2B, 3A, and 3B, a cross-sectional view of the multiple balloon assembly 40 of a medical device 10 is provided. In FIGS. 2A and 2B, the multiple balloon assembly depicted in the medical device of FIG. 1A is described, while in FIGS. 3A and 3B the multiple balloon assembly depicted in the medical device of FIG. 1B is described. In FIGS. 2A and 3A, the multiple balloon assembly 40 is shown in a collapsed state, while the same multiple balloon assembly 40 is shown in FIGS. 2B and 3A, respectively, in an expanded state within a body lumen 90. The outer balloon 65 is disposed around an inner balloon 95. The outer balloon 65 and the inner balloon 95 both have a first end 96, 97 and a second end 98, 99, respectively. The first end 96 of the outer balloon 65 is in communication with a therapeutic agent delivery lumen 100 in the catheter 15, while the first end 97 of the inner balloon 95 is in communication with an injection lumen 105 in the catheter 15. The second end 98 of the outer balloon 65 and the second end 99 of the inner balloon 95 are in contact with the wire guide lumen 22.

Figure 3B:
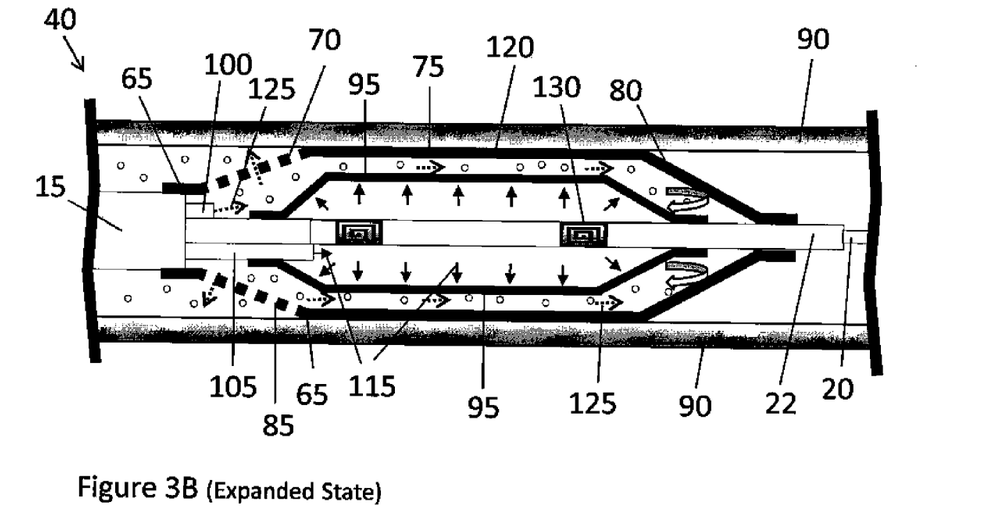
FIG. 3B is a cross sectional view of the multiple balloon assembly of the medical device of FIG. 1B shown in an expanded state according to another aspect of the present disclosure.

The medical device 10 is inserted or deployed into the body lumen 90 in its collapsed state as shown in FIGS. 2A and 3A. The multiple balloon assembly 40 may be deployed by translating the multiple balloon assembly 40 over the guide wire 20 inside of the catheter 15 to the target site. During such deployment, the bodily fluid is freely allowed to flow 110 around the multiple balloon assembly 40 and through the body lumen 90. Upon reaching the target site, a fluid is forced to flow 115 through the inflation lumen 105 into the region between the wire guide lumen 22 and the inner balloon 95 causing the inner balloon 95 to inflate to an expanded state as shown in FIGS. 2B and 3B. The inflation fluid may be any known fluid to one skilled-in-the-art to perform such a function, including but not limited to air or a 50/50 saline/contrast solution. The material, geometry, and configuration of the inner balloon 95 are selected to withstand an internal inflation fluid pressure of about 4 atmospheres to about 30 atmospheres without any leakage or rupture. The thickness of the inner balloon 95 is selected to withstand the force necessary to inflate the inner balloon 95 and to urge the outer balloon 65 against the inner wall of the body vessel 90 without rupturing.

The inflation of the inner balloon 95 forces the middle region 75 of the outer balloon 65 to contact the inner wall 120 of the body vessel 90. The proximal taper region 70 and the distal taper region 80 of the outer balloon 65 preferably do not make contact with the inner wall 120 of the body vessel 90. The contact between the middle region 75 of the outer balloon 65 and the inner wall 120 of the body vessel 90 occludes the flow 110 of fluid through the body vessel 90.

The maximum cross-sectional area of the middle region 75 of the outer balloon 65 that contacts the inner wall 120 of the body vessel 90 is preferably large enough to dilate a portion of the body vessel 90 when the multiple balloon assembly 40 is in its expanded state. The diameter of the outer balloon 65 in its expanded state may vary depending upon the type of body vessel 65 and medical procedure being utilized. For example, when the multiple-balloon assembly 40 is configured for use in a peripheral blood vessel, in a coronary vasculature, or in a bile duct, the diameter of the outer balloon 65 may be within the range of about 1.5-30.0 mm, about 1.5-4.0 mm, and about 5.0-15.0 mm, respectively.

The therapeutic agent is allowed to flow 125 from the delivery lumen 100 in the catheter 15 to a location that is between the inner balloon 95 and outer balloon 65 and finally through the plurality of apertures 85 located in either the distal taper portion 80 (FIG. 2B) or the proximal taper portion 70 (FIG. 3B) of the outer balloon 65 into the body lumen 90. Since the flow 110 of bodily fluid has been occluded by the contact between the middle region 75 of the outer balloon 65 and the inner wall 120 of the body lumen 90, the flow 125 of therapeutic agent can only proceed to the targeted site. In other words, any loss of the therapeutic agent to regions outside of the targeted site is prevented from occurring. Preferably, the geometry, material, and configuration of the outer balloon 65 are selected to withstand an internal pressure of delivering the therapeutic agent and the inflation of the inner balloon 95 without any rupture.

The selection of whether the apertures 85 are located in the distal taper region 80 or the proximal taper region 70 of the outer balloon 65 may be determined according to the location of the targeted site. If the targeted site is downstream in the body lumen 90 from the multiple balloon assembly 40, then the apertures 85 would preferably be located in the distal taper region 80 of the outer balloon 65. However, if the targeted site is upstream in the body lumen 90 from the multiple balloon assembly 40, then the apertures 85 would preferably be located in the proximal taper region 80 of the outer balloon 65.

According to one aspect of the present disclosure, the shape of the inner balloon 95 and the outer balloon 65 can be varied. One skilled-in-the-art will understand that the length of the middle region 75 of the outer balloon can be any length as long as it is configured to effectively occlude the flow of fluid in the body vessel 90 when the multiple balloon assembly 40 is in an expanded state. Preferably, the middle section 75 of the outer balloon 65 is at least equal in length to the length of the inner balloon 95. The overall length of the multiple balloon assembly 40 may range between about 10-60 mm.

The catheter 15 of the multiple balloon medical device 10 can have any suitable dimension, but is preferably shaped and configured for its intended use in a body vessel 90. The catheter 15 preferably includes the wire guide lumen 22 configured to house a guide wire 20. This lumen 22 may have an inner diameter ranging from about 0.33 mm to 1.0 mm with about 0.46 mm being preferred. The overall length of the catheter 15 may vary, but is usually within the range of about 80 to 280 centimeters. The catheter 15 can optionally be configured as a rapid exchange catheter, such as the catheters described in U.S. Pat. Nos. 5,690,642 and 5,814,061. The outside diameter of the catheter 15 may also vary from about 1.0 to 3.5 millimeters with the range of about 1.0 to 1.5 millimeters being preferred. The catheter 15 may also include one or more conventional fittings and/or adaptors located between the manifold 35 and the proximal region 30 of the catheter 15. Further details regarding the manufacturing and/or assembly of a catheter 15 is described in U.S. PCT Application No. PCT/2008/075970 filed on Sep. 11, 2008, and U.S. patent application Ser. No. 12/411,106 filed Mar. 25, 2009, which are hereby incorporated in their entirety by reference.

The catheter 15 may be formed from any thermoformable material that can encase one or more tubular lumens (e.g., inflation, therapeutic agent delivery, and wire guide lumens). The thermoformable material may be selected as one from the group of high density polyethylene (HDPE), polytetrafluoroethylene (PTFE), polyethylene terephthalate (PET), polyester, polyether block amide (PEBA), polyurethane, polyimide, polyolefin, nylon, and any combination or copolymer thereof. The lumens are typically made from a material that has a higher melting temperature than the thermoformable material. Preferably the lumens are made from a polymer, such as a fluorinated hydrocarbon (e.g., PTFE or FEP) or a polyimide, a metal (e.g., Nitinol, titanium, and the like), a composite, or a laminate. The thickness of each lumen is configured to prevent rupturing during inflation and/or delivery of the therapeutic agent. According to one aspect of the present disclosure, an exemplary catheter 15 configuration includes a delivery lumen 100 having a rupture pressure of about 2.7 to 3.5 MPa (27-35 atmospheres). The catheter 15 may optionally include a stiffening member to enhance the slideability and movement of the multiple balloon assembly 40 through the catheter 15.

The plurality of apertures 85 in the distal taper region 80 or the proximal taper region 70 of the outer balloon 65 can be any suitable size and shape configured to provide a desired rate of therapeutic agent release from the outer balloon 65 into the body vessel 90. The apertures 85 are preferably larger than the diameter of any embolization particles present in the therapeutic agent. Although the plurality of apertures 85 may differ in their geometry and size, it is preferred that the apertures 85 have a uniform dimension of about 10 micrometers (0.0004 inch) to about 0.5 mm (0.02 inch). In order to decrease resistance to the release of a therapeutic agent into the body vessel 90, the apertures 85 may increase in cross-sectional area and/or in frequency as they get closer to the distal end of the distal taper region 80 or the proximal end of the proximal taper region 70. The apertures 85 can be formed by any suitable method including, but not limited to mechanical punching, laser cutting, and the like.

The inner balloon 95 and the outer balloon 65 may be formed, molded, or extruded from any flexible, expandable, biocompatible, medical grade polymer. Preferably, the inner balloon 95 and the outer balloon 65 are made from polymers that have a similar Young's modulus and ability to expand. For example, the balloons 95, 65 may be comprised of polyamide (e.g., nylon 12), polyamide block copolymer (e.g., PEBA), polyamide & polyamide copolymer blend (e.g., nylon 12/PEBA and PEBAIPEBA), polyolefin, polyester (e.g., poly(ethylene terephthalate), PET); polyurethane copolymer with MOI, HMOI or TOI hard segment and aliphatic polyester, polyether or polycarbonate soft segment (e.g., Pellethane, Estane or Bionate), and polyester copolymer with 4GT (PBT) hard segment and aliphatic polyester or polyether soft segment (e.g., Hytrel, Pelprene, or Arnitel). The balloons 95, 65 may also be comprised of any other medical grade polymers suitable for use in forming catheter balloons. The inner balloon 95 is non-porous, while the outer balloon 65 includes a plurality of apertures 85 in its distal taper region 80.

The attachment of the inner balloon 95 to the wire guide lumen 22 and the inflation lumen 105, as well as the attachment of the outer balloon 65 to the catheter 15 and the wire guide lumen 22 can be done in any suitable manner. Typically, the inner surfaces of the balloons 95, 65 are attached in a manner that creates a seal that prevents any leakage of a fluid. Methods for attaching the balloons 95, 65 and creating such a seal include, but are not limited to heat sealing, adhesive application, forced convection heating, radio frequency heating, ultrasonic welding, and laser bonding.

Shrink tubing can optionally be used as a manufacturing aid to compress and fuse each balloon 95, 65 to the catheter 15, wire guide lumen 22, or inflation lumen 105. The shrink tubing can be either removed after each balloon 95, 65 is sealed, or remain in position as part of the connected structure. If the catheter 15 or one of the lumens 22, 105 includes a protective or functional outer coating, the balloons 95, 65 may be bonded to the coating.

The therapeutic agent can be introduced through the delivery lumen 100 at a pressure effective to deliver the therapeutic agent into the body vessel 90 through the plurality of apertures 85 that are located in either the distal taper region 80 or proximal taper region of the outer balloon 65. The therapeutic agent can be any suitable agent in fluid form or dispersed in a fluid carrier. For example, the therapeutic agent may be an antisense compound to treat or prevent restenosis; an embolization agent used in the treatment of various forms of cancer; an antithrombotic agent, such as an anticoagulant, antiplatelet, or fibrinolytic agent; a chemotherapeutic agent; a gene therapy agent; an alcohol; or a diagnostic agent (e.g., contrast media), among other bioactive agents. Other examples of therapeutic agents include those described in U.S. Pat. No. 7,094,765, U.S. Patent Publication No. 2006/0269587, and U.S. Patent Application No. 61/093505 filed on Sep. 2, 2008, all of which are incorporated herein in their entirety by reference.

An embolization agent as used herein refers to a particle containing an agent useful for the treatment of diffuse diseases in a targeted tissue vessel of a patient for localized tumor destruction. The embolization agent may comprise an inner core of a chemotherapy drug having a diameter less than a predetermined size for the opening in the targeted tissue vessel and an outer layer of an erodible embolization material encompassing the inner core. The outer layer has an initial diameter that occludes the initial opening in the targeted tissue vessel. During the treatment of the disease, the outer layer of embolization material erodes at a predetermined rate, enhancing penetration of the chemo-embolization agent into the opening of the targeted tissue vessel. The inner core of chemotherapy drug disperses into the targeted tissue vessel after becoming exposed by the erosion of the embolization material of the outer layer. In the present disclosure, the apertures 85 in the distal taper region 80 or proximal taper region 70 of the outer balloon 65 are sized to allow the embolization agent including both the inner core and outer layer to freely flow at a predetermined rate into the body vessel.

Diagnostic agents as used herein are usually necessary to enhance the contrast between various body components and medical devices inserted into a body vessel, when performing an imaging technique, such as x-ray, magnetic resonance, or ultrasound. Examples of useful contrast agents include, but are not limited to barium and iodinated compounds as used for x-ray imaging, compounds and elements having unpaired electrons (e.g., metal ions, metal oxides or the like) for use in magnetic resonance imaging, and solid particles, emulsified liquid droplets, or gas filled bubbles for use in ultrasonic imaging.

Optionally, the multiple balloon assembly 40 of the catheter 15 can include a radiopaque or an echogenic material as a marker band 130 to provide a means for locating the multiple balloon assembly 40 within a body vessel 90. For example, the catheter 15 can include one or more marker bands 130 annularly disposed around the outside of the wire guide lumen 22 and within the inner balloon 95. These marker bands 130 can be used by a clinician to fluoroscopically or ultrasonically view and locate the distal portion of the multiple balloon assembly 40 at the target site within a body vessel 90. Such markers 130 can be constructed by encapsulating a radiopaque or echogenic material, such as a metallic ring, within the wire guide lumen 22 or alternatively using a polymer having a radiopaque or echogenic filler (e.g., barium sulfate, bismuth trioxide, or tungsten). The radiopaque or echogenic material can comprise any suitable opacifying agent, further including bismuth, tantalum, or other suitable agents known in the art. The concentration of the agent in the coating can be selected to be adequately visible under fluoroscopy or ultrasound.

According to another aspect of the present disclosure, the outer surface of the inner balloon 95, the inner surface of the outer balloon 65, or the outer surface of the outer balloon 65 may further include a coating of a bioactive agent, such as an antithrombotic agent. The bioactive coating is designed to release the bioactive agent when the multiple balloon assembly 40 is inflated to its expanded state.

Figure 4:
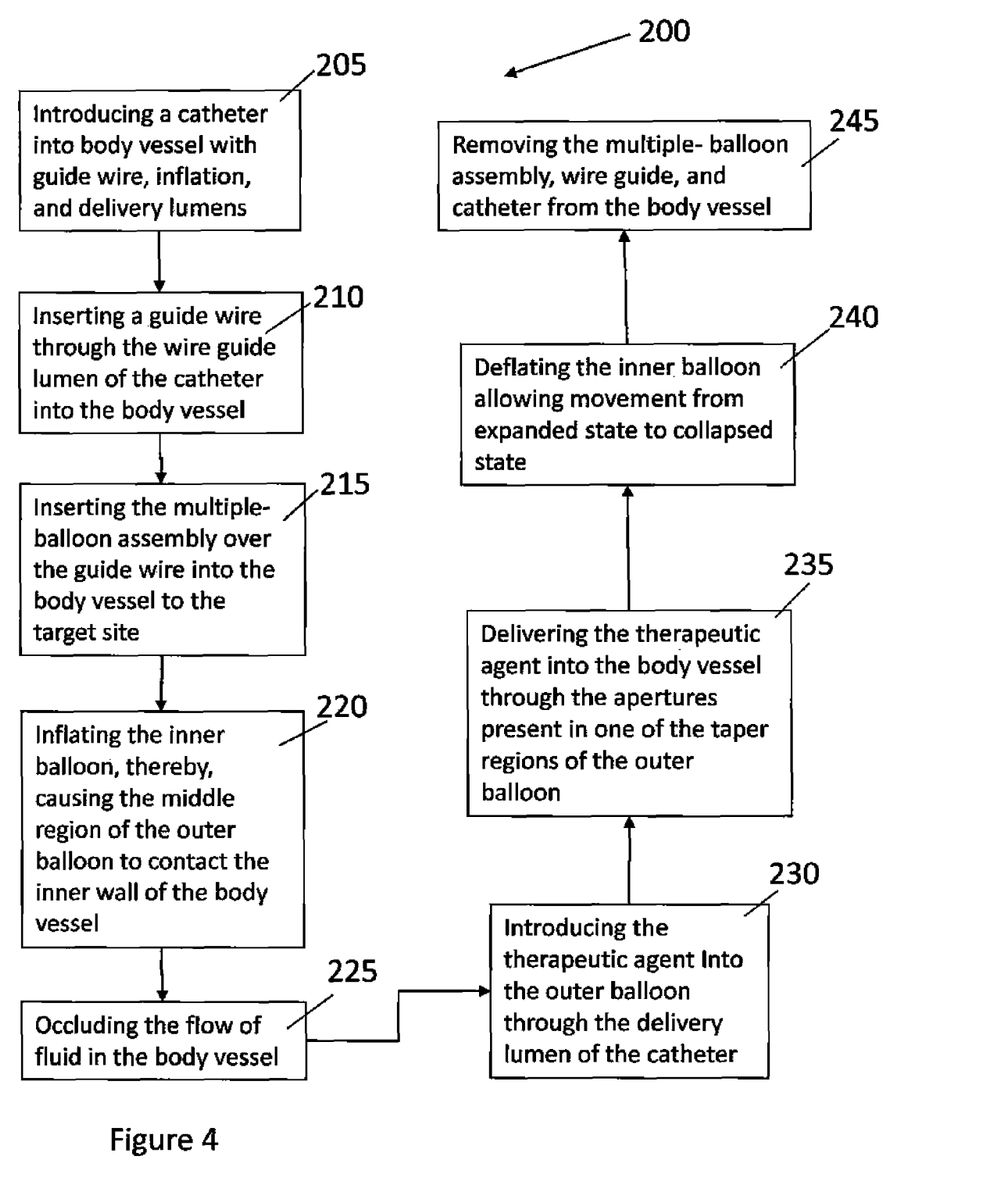
FIG. 4 is a flow chart of a method for delivering a therapeutic agent to a target site within a body vessel using the medical device of FIGS. 1A or 1B according to one embodiment of the present disclosure.

It is another objective of the present invention to provide a method of delivering a therapeutic agent to a target site within a body vessel using the multiple balloon medical device 10 as described herein. Referring to FIG. 4, the method 200 comprises the steps of inserting 205 a catheter having a wire guide lumen, an inflation lumen, and a therapeutic agent delivery lumen into the body vessel. Then a guide wire can be inserted 210 into the body vessel through the wire guide lumen. A multiple balloon assembly is then inserted 215 into the body vessel over the wire guide. The multiple balloon assembly may incorporate a rapid exchange system, a short wire system, or an over-the-wire system. The multiple balloon assembly is slideably translated over the guide wire to a location in the body vessel that is proximate to the target site. The multiple balloon assembly is deployed in its collapsed state.

The inner balloon is then inflated 220 to its expanded state. An inflation fluid can be delivered to the inner balloon through the inflation lumen. The inflation of the inner balloon causes the middle region of the outer balloon to contact the inner wall of the body vessel. The middle region is configured to occlude 225 the flow of fluid within the body vessel when it makes contact with the inner wall of the body vessel. The proximal taper portion and the distal taper portion of the outer balloon are configured to minimize the contact of these regions with the wall of the body vessel.

The therapeutic agent is then introduced 230 through the delivery lumen of the catheter into the outer balloon. The therapeutic agent is introduced 230 at a pressure effective to deliver 235 the agent into the body vessel through the plurality of apertures located in either the distal taper region or the proximal taper region of the outer balloon.

Upon complete delivery of the therapeutic agent to the targeted site, the inner balloon 95 is deflated 240 allowing the multiple balloon assembly 40 to move from the expanded state to a collapsed state. Once the multiple balloon assembly 40 is in its collapsed state, the removal 245 of the medical device 10 from the body lumen 90 is possible.

The foregoing description of various embodiments of the present invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A multiple balloon assembly located in the distal region of a medical device having a catheter that defines an inflation lumen, a therapeutic agent delivery lumen, and a wire guide lumen, the multiple balloon assembly capable of delivering a therapeutic agent into a body vessel, the body vessel having bodily fluid and an inner wall, the multiple-balloon assembly comprising:

an inner balloon having a first end and a second end, the first end being in contact with both the wire guide lumen and the inflation lumen, the second end being in contact with only the wire guide lumen, the inner balloon being in communication with the inflation lumen and adapted to move between a collapsed state and an expanded state; and an outer balloon having a first end and a second end, the outer balloon being disposed around the inner balloon, the outer balloon being in communication with the therapeutic agent delivery lumen and defining a proximal taper region, a middle region, and a distal taper region; the proximal taper region including the first end of the outer balloon being in contact with the catheter; the middle region being in contact with the inner balloon when the inner balloon is in the expanded state; the distal taper region including the second end of the outer balloon being in contact with the wire guide lumen; only the proximal taper region of the outer balloon having a plurality of apertures adapted to allow for the therapeutic agent to be delivered into the body vessel, wherein in the expanded state the plurality of apertures are out of communication with the inner wall of the body vessel;

wherein the movement of the inner balloon to the expanded state forces the middle region of the outer balloon to contact the wall of the body vessel and to occlude the flow of fluid through the vessel.

2. The multiple balloon assembly according to claim 1, wherein the inner balloon is non-porous and configured to withstand an internal inflation fluid pressure of about 4 atmospheres to about 30 atmospheres without leaking or rupturing.

3. The multiple balloon assembly according to claim 1, wherein the proximal taper region and the distal taper region of the outer balloon are configured such that they do not make contact with the inner wall of the body vessel when the middle region makes contact with said inner wall of the body vessel.

4. The multiple balloon assembly according to claim 1, wherein the cross-sectional area of the middle section of the outer balloon that contacts the inner wall of the body vessel is large enough to dilate a portion of the body vessel.

5. The multiple balloon assembly according to claim 1, wherein each aperture is sized and shaped to provide a predetermined rate of therapeutic agent release from the outer balloon into the body vessel.

6. The multiple balloon assembly according to claim 5, wherein each aperture has a diameter ranging from about 10 micrometers (0.0004 inch) to about 0.5 mm (0.02 inch).

7. The multiple balloon assembly according to claim 5, wherein the therapeutic agent is one selected from the group of embolization agents, chemotherapy agents, gene therapy agents, alcohols, and diagnostic contrast agents.

8. A method for delivering a therapeutic agent into a body vessel, the body vessel having bodily fluid and an inner wall, the method comprising the steps of:

introducing a catheter into the body vessel, the catheter defining an inflation lumen, a therapeutic agent delivery lumen, and a wire guide lumen;

inserting a guide wire through the wire guide lumen into the body vessel;

inserting a multiple balloon assembly in a collapsed state over the guide wire into the body vessel to a location that is proximate to the target site; the multiple balloon assembly configured to move between a collapsed and an expanded state, the multiple balloon assembly comprising an inner balloon attached to the distal region of the wire guide lumen, the inner balloon being in communication with the inflation lumen, and an outer balloon disposed around the inner balloon and having a proximal taper region, a middle region, and a distal taper region, only the proximal taper region of the outer balloon having a plurality of apertures, wherein in the expanded state the plurality of apertures are out of communication with the inner wall of the body vessel, the outer balloon being in communication with the therapeutic agent delivery lumen;

allowing the multiple balloon assembly to move from the collapsed state to an expanded state by inflating the inner balloon and inner balloon forcing the middle region of the outer balloon to contact the inner wall of the body vessel;

occluding the flow of fluid through the body vessel;

introducing a therapeutic agent through the delivery lumen into the outer balloon;

delivering the therapeutic agent into the body vessel through the apertures present in one of the taper regions of the outer balloon;

deflating the inner balloon allowing the multiple balloon assembly to move from the expanded state to a collapsed state; and removing the multiple balloon assembly from the body vessel.

9. The method according to claim 7, wherein during the step of allowing the multiple balloon assembly to move from the collapsed state to an expanded state, the proximal taper region and the distal taper region of the outer balloon are configured such that they do not make contact with the inner wall of the body vessel.

10. The method according to claim 7, wherein during the step of delivering the therapeutic agent into the body vessel, each aperture is sized and shaped to provide a predetermined rate of therapeutic agent release from the outer balloon into the body vessel.

11. The method according to claim 7, the method further comprising the step of viewing the location of the multiple balloon assembly in the body vessel by identifying a radiopaque or echogenic marker located within the multiple balloon assembly.

12. A multiple balloon medical device extending from a proximal region to a distal region, the medical device being capable of delivering a therapeutic agent into a body vessel, the body vessel having bodily fluid and an inner wall, the medical device comprising:

a catheter defining an inflation lumen, a therapeutic agent delivery lumen, and a wire guide lumen;

an inner balloon attached to the wire guide lumen proximate to the distal region of the device, the inner balloon being in communication with the inflation lumen and configured to move between a collapsed state and an expanded state; and an outer balloon disposed around the inner balloon and having a proximal taper region, a middle region, and a distal taper region, only the proximal taper region of the outer balloon having a plurality of apertures and the outer balloon being in communication with the therapeutic agent delivery lumen, wherein in the expanded state the plurality of apertures are out of communication with the inner wall of the body vessel;

wherein the movement of the inner balloon to the expanded state forces the middle region of the outer balloon to contact the wall of the body vessel and to occlude the flow of fluid through the vessel, the apertures in the taper region of the outer balloon being configured to allow for the therapeutic agent to be delivered into the body vessel.

13. The medical device according to claim 12, the medical device further comprising a manifold located within its proximal region; the manifold including an inflation port in communication with the inflation lumen and a therapeutic agent delivery port in communication with the therapeutic agent delivery lumen.

14. The medical device according to claim 13, wherein the manifold further comprises a wire guide port in communication with the wire guide lumen.

15. The medical device according to claim 12, wherein access to the wire guide lumen is provided by a port opening located in the catheter.

16. The medical device according to claim 12, the medical device further comprising a guide wire disposed within the wire guide lumen.

17. The medical device according to claim 12, wherein the inner balloon is non-porous and configured to withstand an internal inflation fluid pressure of about 4 atmospheres to about 30 atmospheres without leaking or rupturing.

18. The medical device according to claim 12, wherein the proximal taper region and the distal taper region of the outer balloon are configured such that they do not make contact with the inner wall of the body vessel when the middle region makes contact with said inner wall of the body vessel.

19. The medical device according to claim 12, wherein the cross-sectional area of the middle section of the outer balloon that contacts the inner wall of the body vessel is large enough to dilate a portion of the body vessel.

20. The medical device according to claim 12, wherein each aperture is sized and shaped to allow the therapeutic agent to flow from the therapeutic agent delivery lumen into the body vessel at a predetermined rate.

21. The medical device according to claim 20, wherein the therapeutic agent is one selected from the group of antisense compounds, embolization agents, antithrombotic agents, chemotherapy agents, gene therapy agents, alcohols, and diagnostic agents.

* * * * *